United States Patent
Heyman

(10) Patent No.: US 8,353,296 B1
(45) Date of Patent: Jan. 15, 2013

(54) POSITIVE AIRWAY SUPPLY SYSTEM TO NASAL CANNULA

(75) Inventor: Arnold M. Heyman, Los Angeles, CA (US)

(73) Assignee: Neotech Products, Inc., Valencia, CA (US)

( * ) Notice: Subject to any disclaimer, the term of this patent is extended or adjusted under 35 U.S.C. 154(b) by 426 days.

(21) Appl. No.: 12/658,721

(22) Filed: Feb. 16, 2010

(51) Int. Cl.
*A61M 15/08* (2006.01)

(52) U.S. Cl. .................................................. 128/207.18

(58) Field of Classification Search ............ 128/207.18, 128/206.11, 207.11, 207.13, 207.17
See application file for complete search history.

(56) References Cited

U.S. PATENT DOCUMENTS

| | | | | |
|---|---|---|---|---|
| 5,271,391 A | * | 12/1993 | Graves | 128/207.18 |
| 2005/0028823 A1 | * | 2/2005 | Wood | 128/207.18 |

* cited by examiner

*Primary Examiner* — Christopher D Koharski
(74) *Attorney, Agent, or Firm* — William W. Haefliger

(57) ABSTRACT

A nasal cannula fitting, comprising in combination, a rigid plastic tubular first duct configured to directly endwise connect with apparatus assisting respiratory air, a relatively flexible plastic second duct fitting onto an end portion of the first duct, relatively flexible third plastic ducts integral with the second duct and diverging endwise therefrom to receive flow of the assistance air, and nasal cannula plastic tubing connected in series with the respective third ducts. Nasal prongs on the cannula tubing may carry pressure sealing toggling skirts.

11 Claims, 2 Drawing Sheets

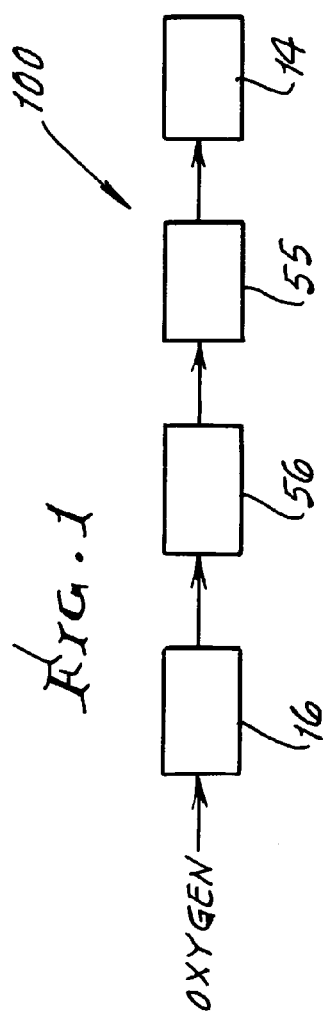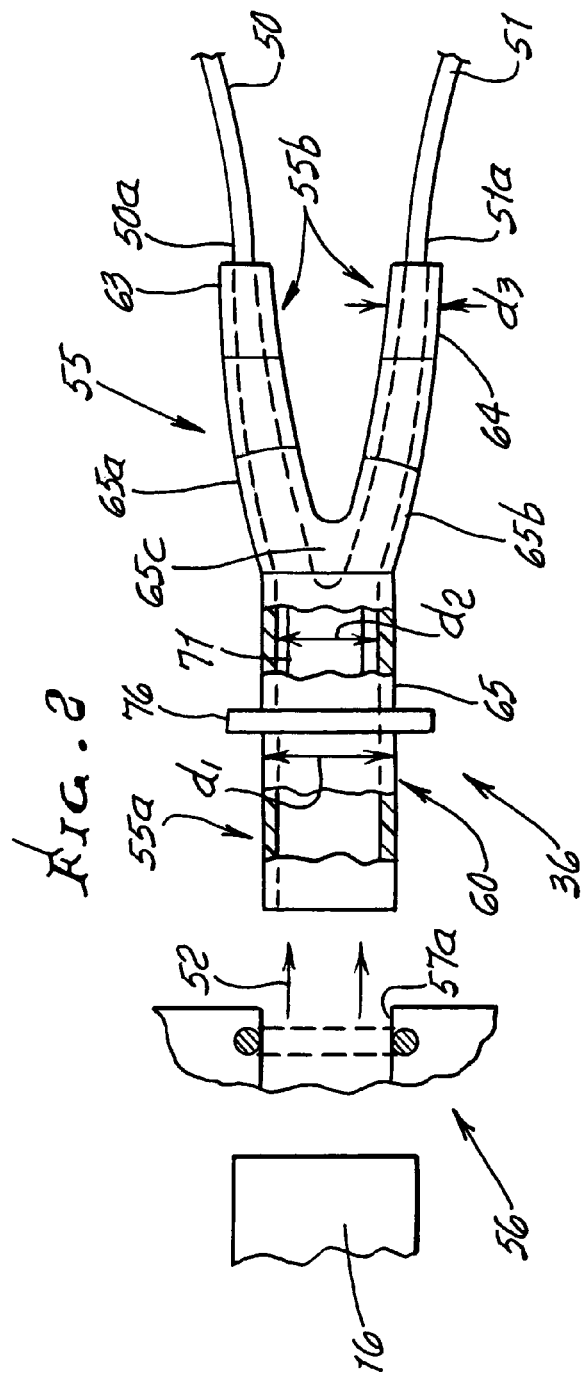

POSITIVE AIRWAY SUPPLY SYSTEM TO NASAL CANNULA

BACKGROUND OF THE INVENTION

Figure 3:
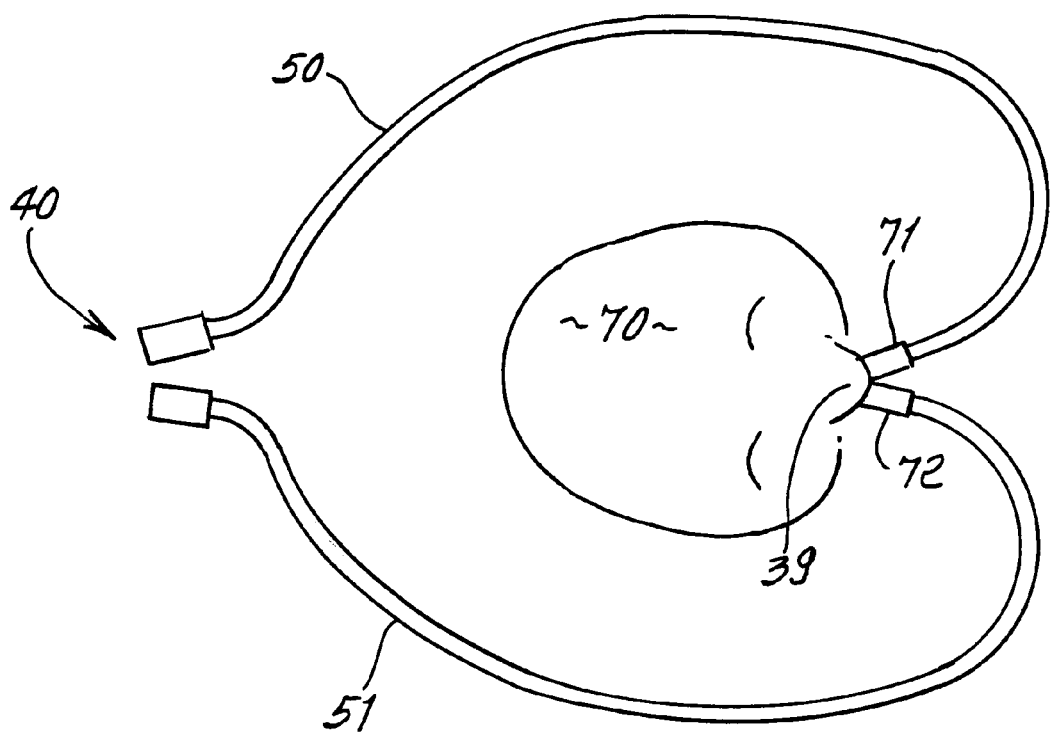

This invention relates generally to nasal cannula therapy, and more particularly to improvements concerning tubing flow in nasal cannula therapy systems.

Nasal continuous positive airway pressure, NCPAP, is a standard method for administration of non-invasive positive airway pressure in the Neonate. Historically, Nasal cannulae have been used during infant weaning from invasive ventilation. Mechanical Ventilators (MV) with their attached ventilator circuits (VC) have been the standard for delivering Nasal Continuous Positive Airway Pressures (NCPAP). The disadvantage of this system has been the type of devices that are used to interface with the patient and the VC. These devices apply pressure to the nares and septum of the nose in order to diminish the leak that occurs between the prongs of the cannula and the nares. This pressure against the nares is exceptionally deleterious to the newborn and may cause traumatic changes to the nose which may be disfiguring and permanent. These devices held the promise of improved humidification and warming of the cannula flows, but introduced the possible deleterious effect of unknown pressure propagation as well as reported bacteria contamination of the circuit.

Accordingly, there was concern about delivering pressures that were excessive and with possibly damage to the respiratory tract, sinuses, eardrum or GI tract. Mechanical ventilators may be used for NCPAP to control pressures.

In order to overcome this potential, nasal canulae are presently being used without MV and VC. This system uses blended air and oxygen with humidification and heat without the MV attached to nasal cannulae which are inserted atraumatically into the nostrils. These devices held the promise of improved comfort and decreased nursing care, but introduced the possible deleterious effect of unknown pressure propagation. There was concern about delivering pressures that were excessive and with possible damage to the respiratory tract, sinuses, eardrum or GI tract

SUMMARY OF THE INVENTION

It is a major object of the invention to provide a solution to the above problems and difficulties, and to provide a simple, reliable connection or connections between air supply means and nasal cannula tubing.

Basically, the invention includes:

a) a rigid plastic tubular first duct configured to directly endwise connect with a ventilatory circuit to the mechanical ventilator, b) a relatively flexible plastic second duct fitting onto an end portion of said first duct, c) relatively flexible third plastic ducts integral with the second duct and diverging endwise therefrom to receive flow of said assistance air, d) and nasal cannula plastic tubing connected in series with the respective third ducts.

A further object includes provision for penetration by the first rigid duct into the flexible second duct to terminate proximate flow entrance ends of the third ducts. Typically, the third ducts have bore diameters $d_3$ which are substantially less than the bore diameter of said first duct.

In addition, the second duct preferably clasps penetrating rigid extent of the first duct; and the first duct has overall length substantially exceeding the overall length of the second duct enabling rapid push-in connection of the first duct into an air supplying exit from apparatus that delivers respiratory air.

Yet another object includes provision of an inflexible radially extending flange on and integral with the first duct, the entirety of the second duct located at one side of the flange. In this regard, the source of respiratory air flow typically has an exit penetrated by first duct extent located at the opposite side of said flange.

An added object is to provide the first, second and third ducts in an easily and usably manipulated Y-shaped configuration. In this regard the first and second ducts preferably have outer diameters merging with the outer diameters of the third ducts.

A further object is to provide a) a Y-shaped tubular adapter having a stem portion connectable to a mechanical ventilator, and two divergent tubular portions connected to elongated cannalae, b) there being nasal prongs connected with said cannula, and said prongs carrying sealing skirts for nasal sealing.

These and other objects and advantages of the invention, as well as the details of an illustrative embodiment, will be more fully understood from the following specification and drawings, in which:

DRAWING DESCRIPTION

Figure 3A:
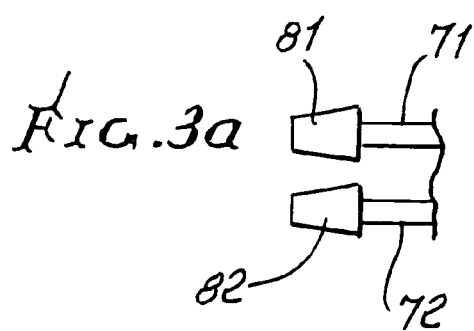

FIG. 1 is a system diagram;
FIG. 2 is a detailed view of an air conductor;
FIG. 3 shows use of the apparatus; and
FIG. 3a shows nasal prong skirts.

DETAILED DESCRIPTION

In FIG. 1, the system 100 supplies warm air, or oxygen blended with air, heated to humidified to nasal passages at 14, adjacent the head of an infant, or other air recipient. Elements of the system include:

16—mechanical ventilator
56—ventilator circuit
55—Y-shaped conductor
14—nasal prongs (cannulae)

FIG. 2 shows a ventilatory circuit 56 from a mechanical ventilator 16 supplying the air or blended air and oxygen, to flow metering apparatus 36, which operates to meter or distribute the pressurized flow into two streams supplied to the two flexible cannula tubings 50 and 51 terminating at the nasal prongs 71 and 72 that fit in nostrils indicated at 39 in FIG. 3. Ventilator circuit 56 is located upstream of a Y-shaped air conductor 55 having flow delivering branches 65a and 65b connected with the flexible plastic cannula looping branches 50 and 51. Conductor 40 is typically located at the rear of the infant's head 70.

Referring now to FIG. 2, it shows:

i) flow metering first means such as ventilator 16 upstream of nasal cannula tubing 50 and 51, ii) the nasal cannula configured to receive the pressurized air stream 52, iii) the nasal cannula including two looping branches 50 and 51 spaced from the air stream supply apparatus 56, the branches having ends 50a and 51a.

iv) a Y-shaped conductor 55 connected with the cannula ends 50a and 51a, and being in communication with the air stream, v) the Y-shaped conductor 55 having an inflexible air entrance region 55a, and a flexible air exit region or regions 55b, whereby region 55a is readily plug-in connectable to air supply apparatus 56 (such as a ventilator circuit), as at fixed position receptacle 57a, and whereby region 55b readily flexes with or flexibly accommodates to, the flexible tubular cannula.

More specifically, the conductor 55 includes a rigid tubular plastic stem 55a having external diameter matching or approximately matching a diameter at 57a. Also, the conductor includes two divergent flexible plastic ends 63 and 64 carried by the stem, and having a single integral extension 65, aligned with stem 60, and which is enlarged to form an inlet diameter $d_2$. Extension 65 has branches 65a and 65b which merge at intermediate region 65c, and from which ducts 63 and 64 diverge, in downstream directions, as shown, whereby cannula branches 50 and 51 are flexibly directed divergently, as shown in FIG. 3, to extend about the infant's (or other wearer's) head 70. Each duct 63 and 64 has a reduced outlet diameter $d_3$ remote from $d_1$ and $d_2$.

As shown, the enlarged inlet end or extension 65, consisting of the same flexible material of ducts 63 and 64, is stabilized by fitting over a rigid plastic internal stabilizing tube 71 carried by and fitting within the rigid stem 60, to project rightwardly beyond an external flange 76 on the stem. The projecting extent of the tube projects beyond the stem, and carries the enlarged inlet end of the flexible extension 65, in such manner that the end of 65 fits endwise against the flange 76, thereby positively positioning the flexible and inflexible elements of the conductor, to best usage and assembly and to prevent air leakage. Typically the inlet end of the extension 65 is radially stretched over the stabilizing tube 71 blocking air leakage.

FIG. 3 shows the cannula tubings 50 and 51 extending or looping from conductor tubings 63 and 64, about the head of an infant, and to the nasal prongs 71 and 72. The latter may have attached conical skirts 81 and 82 that toggle and seal against nasal passages, blocking escape of supplied air. see FIG. 3a The external diameter $d_1$ of the stem 60 is typically about 15 mm to readily plug in opening 57a of the ventilator circuit.

I claim:

1. A nasal cannula fitting, comprising in combination,
a) a rigid plastic tubular first duct configured to directly endwise connect with a ventilator circuit providing respiratory assistance air,
b) a relatively flexible plastic second duct fitting onto an end portion of said first duct,
c) relatively flexible third plastic ducts integral with the second duct and diverging endwise therefrom with Y configuration to receive flow of said assistance air, the first and second ducts overlapping whereby the second duct terminates proximate flow entrance ends of the third ducts,
d) and nasal cannula plastic tubing connected in series with and penetrating the respective third ducts to extend therefrom,
e) there being an inflexible radially extending flange on and integral with the first duct, the entirety of the second duct located at one side of the flange, and between and closely proximate both the flange and said Y configuration of the third plastic ducts, and wherein the flexible second duct is in circumferentially clasping relation with rigid extent of the first duct,
f) and wherein the third ducts have bore diameters $d_3$ which are substantially less than the bore diameter of said first duct.

2. The combination of claim 1 wherein the first duct has overall length substantially exceeding the overall length of the second duct.

3. The combination of claim 1 including a source of said respiratory air having an exit outlet penetrated by first duct extent located at the opposite side of said flange.

4. The combination of claim 3 wherein said first duct extent has a bore diameter equal to approximately 15 millimeters.

5. The combination of claim 1 wherein said first, second and third ducts define a conforming Y-shaped configuration.

6. The combination of claim 3 wherein the first and second ducts have outer diameters merging with the outer diameters of the third ducts.

7. The combination of claim 1 including nasal prongs connected with said cannula tubing, and toggling skirts on said prongs.

8. The combination of claim 1 wherein
g) there being nasal prongs connected with said cannula tubing, and said prongs carrying sealing skirts for nasal sealing.

9. The combination of claim 8 wherein said skirts consist of plastic material.

10. The combination of claim 9, wherein said skirts are toggling skirts surrounding the prongs.

11. The combination of claim 1 wherein said first duct is sufficiently stiff to be directly plugged into an output opening of a mechanical ventilator.

* * * * *